United States Patent [19]

Sussman et al.

[11] E Patent Number: Re. 33,420

[45] Reissued Date of Patent: Nov. 6, 1990

[54] SYSTEM FOR CONTROLLING AN IMPLANTED NEURAL STIMULATOR

[75] Inventors: Marvin L. Sussman, Miami; Barry M. Yomtov, Cooper City, both of Fla.

[73] Assignee: Cordis Corporation, Miami, Fla.

[21] Appl. No.: 247,131

[22] Filed: Sep. 12, 1988

Related U.S. Patent Documents

Reissue of:

[64] Patent No.: 4,735,204
Issued: Apr. 5, 1988
Appl. No.: 924,743
Filed: Oct. 30, 1986

U.S. Applications:

[63] Continuation of Ser. No. 651,434, Sep. 17, 1984, abandoned.

[51] Int. Cl.[5] ..... A61N 1/36

[52] U.S. Cl. ..... 128/419 R; 128/784

[58] Field of Search ..... 128/419 C, 419 E, 419 P, 128/419 PG, 419 R, 421, 422, 423 R, 784, 785

[56] References Cited

U.S. PATENT DOCUMENTS

| | | | |
|---|---|---|---|
| 3,645,267 | 2/1972 | Hagfors | 128/421 |
| 3,669,120 | 6/1972 | Nielson | 128/419 PG |
| 3,713,449 | 1/1973 | Mulier | 128/419 PG |
| 3,796,221 | 3/1974 | Hagfors | 128/421 |
| 3,830,242 | 8/1974 | Greatbatch | 128/419 PT |
| 3,865,119 | 2/1975 | Svensson et al. | 128/419 PT |
| 4,124,031 | 11/1978 | Mensink et al. | 128/419 PG |
| 4,285,347 | 8/1981 | Hess | 128/785 |
| 4,390,023 | 6/1983 | Rise | 128/421 |
| 4,440,173 | 4/1984 | Hudziak et al. | 128/419 PG |
| 4,538,624 | 9/1985 | Tarjan | 128/419 R |
| 4,649,936 | 3/1987 | Ungar et al. | 128/784 |

FOREIGN PATENT DOCUMENTS

| | | | |
|---|---|---|---|
| 985987 | 3/1965 | United Kingdom | 128/419 G |

*Primary Examiner*—Francis Jaworski
*Assistant Examiner*—George Manuel
*Attorney, Agent, or Firm*—Henry W. Collins; Thomas R. Vigil

[57] ABSTRACT

An improved control system for a neural stimulator allowing either the patient or physician to effect the level of output by application of an external magnet. Such application of a magnet for a predetermined period of time initiates an incrementally increasing output, under control of an implanted microprocessor, allowing human feedback from the patient to determine the effective level of output current to fix the output at the selected effective level.

17 Claims, 2 Drawing Sheets

SYSTEM FOR CONTROLLING AN IMPLANTED NEURAL STIMULATOR

Matter enclosed in heavy brackets [ ] appears in the original patent but forms no part of this reissue specification; matter printed in italics indicates the additions made by reissue.

*This application is a Reissue of application No. 06/924,743 filed on 10/30/86 and issued as U.S. Pat. No. 4,735,204.*

BACKGROUND OF THE INVENTION

1. Field of the Invention

The present invention relates generally to medical electronic apparatus for applying electrical current to living tissue including programmable apparatus for controlling the electrical current applied therein. More particularly, the present invention relates to a system for controlling the current supplied to an implanted electrode within a body for electrically stimulating a nerve.

2. Description of the Prior Art

Implantable apparatus have been developed in recent years which include an electrode implantable within a living body for electrically stimulating a nerve. Such an apparatus is disclosed in U.S. Pat. No. 3,822,708. In this apparatus, an implantable electrode-carrying device is arranged to be positioned on the spinal cord so that an electric current can be passed through an electrode into a portion of the juxtaposed spinal cord area. The passage of the current into the nerve acts to block electrical pain signals.

More recently, there has been described in U.S. Pat. No. 4,323,073 an apparatus for controlling the direct current applied to living tissue and a method for increasing the current to a predetermined level for a period of time and then decreasing the current. In this manner, no nerve reaction or spasm is caused while the appropriate stimuli is provided for the reduction of pain. This method, however, provides only an automatically modulated output at only one or two levels and does not provide for patient or physician control of the level of stimulation.

Implantable cardiac pacers have utilized programmable devices to establish a desired output in response to transmitted programming signals. Such a device is described in U.S. Pat. No. 4,253,466, where a radio frequency transmitter is used to program an implanted pacemaker. Once programmed, a magnetic field actuated reed relay is used to provide temporary reprogramming and is operable to reset the output to the original setting when the magnetic field is removed.

SUMMARY OF THE INVENTION

According to the teaching of the present invention, there is provided a system for controlling an implanted neural stimulator by an externally applied magnetic means. With this system a timing cycle is permanently programmed within an implanted microprocessor to interact with a magnetically actuated reed relay for selective alteration of the amplitude of the stimulator output.

A neural stimulator system including electrode to nerve electrical connections and circuitry as discussed in the prior art (U.S. Pat. Nos. 3,896,817 and 3,841,306) are implanted in a patient. A microprocessor is also implanted beneath the skin of the patient to control the neural stimulator and is programmed to provide a desired output range. The programmed microprocessor monitors the status of a magnetically controlled reed switch implanted proximate the skin surface of the patient to select a desired output. Application of a magnet to the surface of the skin closes the reed switch and this closure is sensed by the microprocessor. If the magnet is removed and the reed switch reopens within a short time, such as within a 0.003 second to 1 second time period, the neural stimulator is turned to the "on" state. The application of the magnet over the reed switch for a second period of time, such as from 2 to 6 seconds, will be sensed by the microprocessor as an instruction to turn the neural stimulator to the "off" state. Application of the magnet for a third period of time, such as some period greater than 6 seconds, causes the output generated by the neural stimulator to increase incrementally from zero up to a preprogrammed maximum output. At a point where the patient and physician determine that the magnitude of the stimulation is sufficient, the magnet is removed and the generated output remains at the level attained at the time of the magnet removal. Such controllability has been found to be highly desirable since neural stimulation can be lost and pain may return when a patient changes positions. In such an instance, the patient can apply the magnet over the implanted neural stimulator to increase the output to a higher selected level to remove the pain.

DESCRIPTION OF THE PREFERRED EMBODIMENT

Figure 1:
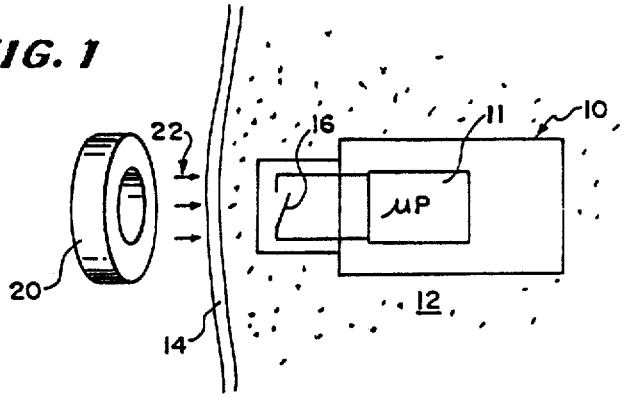
FIG. 1 is a partially perspective mechanical and partially schematic view of a magnet adjacent an implanted megnetically controlled microprocessor which is actuated by an implanted reed switch for controlling a neural stimulator.

Referring now to FIG. 1, there is illustrated therein an implanted neural stimulating apparatus 10 including a microprocessor 11. The microprocessor 11 is implanted within living tissue 12 beneath the skin 14 and controls a neural stimulator including electrodes for carrying electrical current to the nerves in accordance with commonly known principles of neural stimulation. A neural stimulator and an electrode for implantation in a spine adjacent a spinal cord are old in the art. See Hagfors U.S. Pat. No. 3,645,267 issued Feb. 29, 1972 and Hess U.S. Pat. No. 4,285,347 issued Aug. 25, 1981, the disclosures of which are incorporated herein by reference. Electrically coupled to the microprocessor 11 and implanted within the tissue 12 proximate the skin 14 is a magnetically actuated reed switch 16. The reed switch 16 is controlled and switched from its open state to its closed state through application of an external magnet 20. A magnetic field 22 of the magnet 20 penetrates the skin 14 and the tissue 12 to close the reed switch 16.

Figure 2:
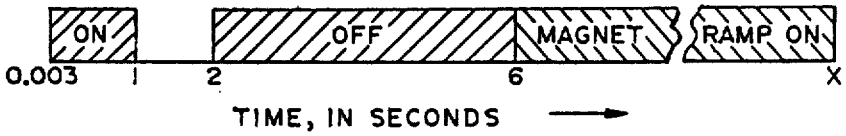
FIG. 2 is a timing diagram of the microprocessor control intervals.

The closing of the reed switch 16 is sensed by the microprocessor 11 and the sensing initiates a timing cycle, as shown in FIG. 2.

If the magnet 20 is removed within a first period of time, such as 0.003 second to 1 second, the reed switch 16 will reopen and the open condition will be sensed by the microprocessor 11 as an instruction to turn the neural stimulator to its "on" state.

If the magnet 20 is held in place for a period of time exceeding 2 seconds but less than 6 seconds and then removed, the reopening of the reed switch 16 within that period of time is sensed by the microprocessor 11 as an instruction to turn the neural stimulator to an "off" state.

In the event the magnet 20 is held in place against the skin for a period of time greater than 6 seconds, this is sensed by the microprocessor 11 as a signal to begin generation of an output signal periodically increasing in magnitude according to a ramp function and referred to as a magnetic ramp 24.

Figure 3:
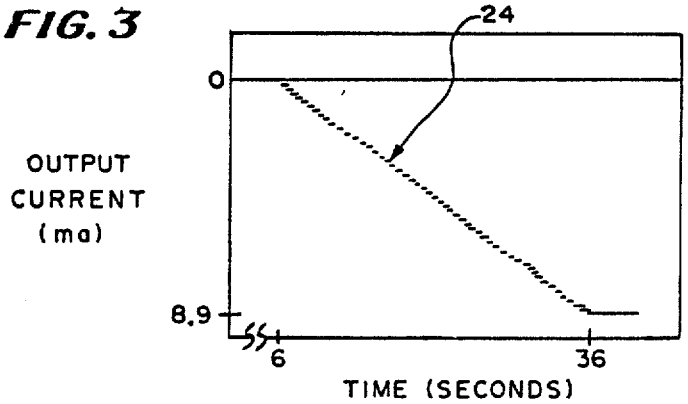
FIG. 3 is a graph of the microprocessor controlled output current versus time.

FIG. 3 is a graph of increasing amplitude of output current (ramp 24) over a period of time. The output current is plotted on the vertical axis increasing from 0 to 8.9 milliamps and the time is plotted on the horizontal axis increasing from 6 seconds to 36 seconds.

Accordingly, if the magnet 20 is held in place for a period greater than 6 seconds but less than 36 seconds, an output current is selected by the microprocessor according to the graph shown in FIG. 3. Microprocessor control of a neural stimulator is old in the art. See the Rise U.S. Pat. No. 4,390,023 issued June 28, 1983, the disclosure of which is incorporated herein by reference.

Figure 4:
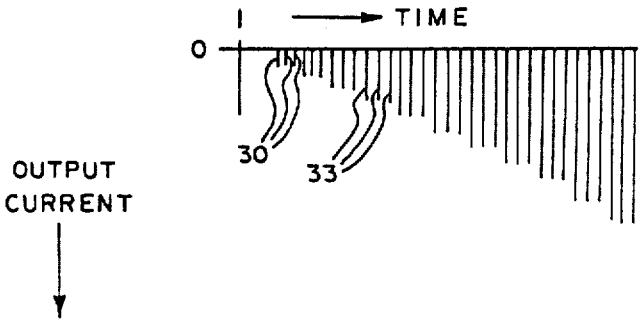
FIG. 4 is an enlarged fragmentary graphical view of the output current pulses shown in FIG. 3.

In the preferred embodiment of the present invention, during the generation of the output current ramp 24, the microprocessor 11 is programmed to periodically increase the output current in increments, such as 0.12 milliamps, each 0.042 second, until the maximum output permanently programmed in the microprocessor is reached. Additionally, the output is generated in a series of three pulses 30, 33, etc. (FIG. 4) such that each burst of three pulses would be incrementally greater than the previous burst.

Heretofore, in the use of certain implantable neural stimulators, the rate of stimulation and the level of output current of amplitude can be changed non-invasively by a physician at implantation or during subsequent office visits. To effect these changes, a totally dedicated device such as a programmer or microprocessor is used. In addition, the patient and/or the physician can activate or de-activate the output of the implanted neural stimulator by the application of a magnet.

However, changes in the patient's position such as from sitting to standing, can cause cessation of efficacious stimulation. In such instances, an office visit to the physician is necessary for re-programming of the implanted neural stimulator to change the output of the stimulator. With the system of the present invention for controlling an implanted neural stimulator, the capability of changing the output current levels within a programmed output current range by use of an externally applied magnet 20 is provided, and the frequency of office visits can be decreased. The patient can then choose that output current level which is most efficacious for both activity level and physical position.

Also, the patient cannot magnetically change the output level to unsafe levels because the physician has preset the maximum output current/amplitude capable of being output by the neural stimulator apparatus 10 controlled by the microprocessor 11

With the neural stimulating apparatus 10 of the present invention, after implantation of the apparatus 10, the physician can program the apparatus to "on" and to a desired rate an output current.

Previously a patient or a physician could turn an implanted neural stimulator to "off" and at a later time to "on" by applying a magnet over the stimulator. When the stimulator was "on", application of the magnet for 2 to 6 seconds would turn the unit "off". Conversely, when the neural stimulator was in "off" mode, the implanted neural stimulator would be turned "on" by application of the magnet for 0.003 to 1 second. The output current and rate would then be those which were programmed by the physician.

In accordance with the teachings of the present invention, addition of the magnetic ramp function (e.g. ramp 24), whose duration is programmed using a dedicated external device by a physician permits the patient and/or the physician to change the output current amplitude. Application of the magnet 20 for periods greater than 6 seconds causes the output current to increase incrementally from 0 to the maximum programmed output current. At a point where the patient and/or the physician determines that the magnitude of the stimulation is efficacious but before the end of the magnetic ramp duration, the magnet 20 is removed and stimulation occurs at that output current level which was obtained at the time of the removal of the magnet 20. The output current 24 will never exceed the maximum current programmed.

When a patient changes position from sitting to standing and finds that neural stimulation is lost, e.g. return of pain, the patient can apply the magnet 20 over the implanted neural stimulating apparatus 10 to increase the output current to a higher level or to a more effective level.

Figure 5:
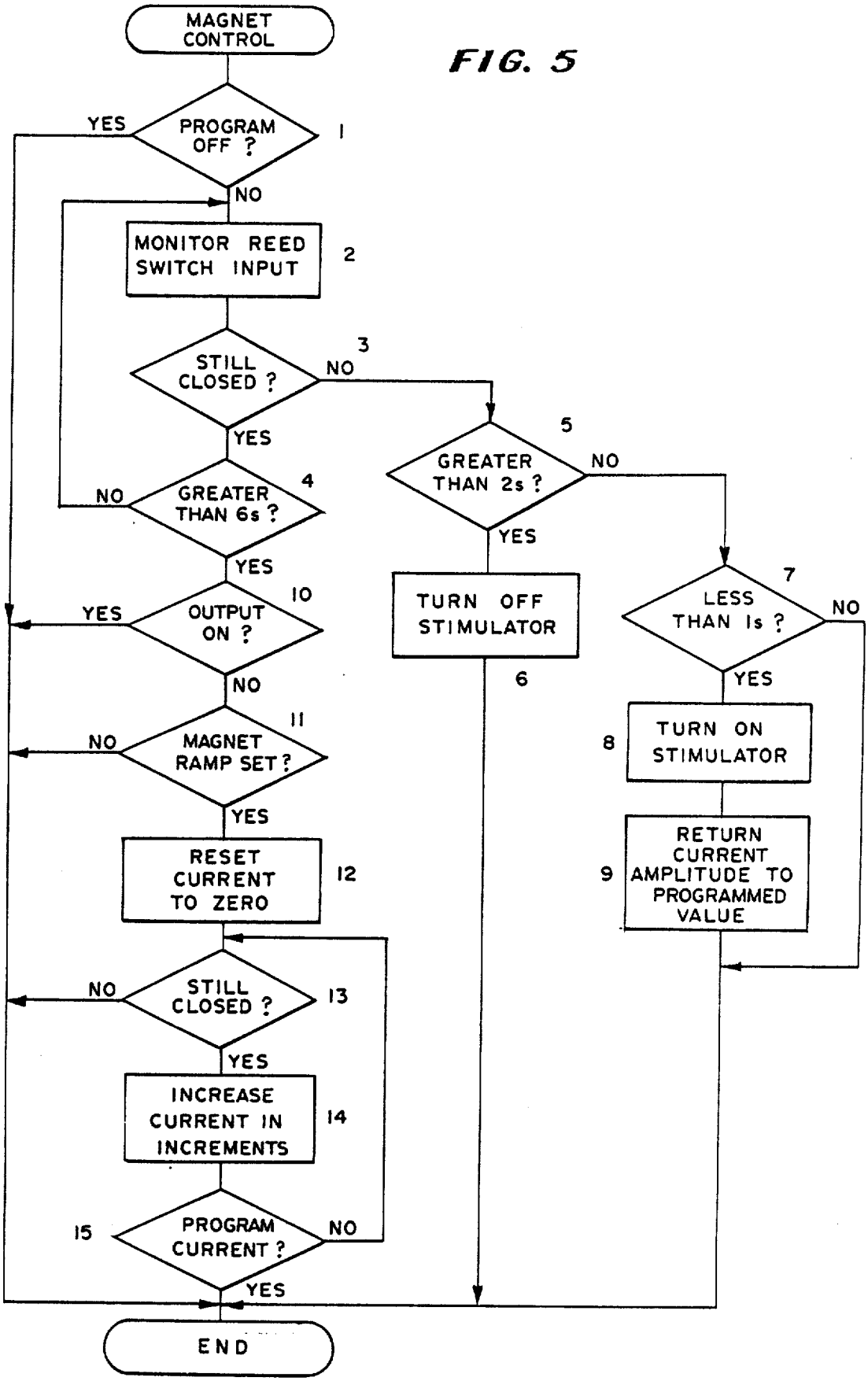
FIG. 5 is a flow chart of the program or protocol of the microprocessor.

The program or protocol carried out by the microprocessor 11 in response to magnet control or positioning of the magnet 20 adjacent to the neural stimulating apparatus 10 is shown in FIG. 5. The steps followed in executing the program are as follows:

STEP 1. At this step the microprocessor 11 determines whether the program is "on" or "off". For example, if the current output was at the maximum level established by the physician the program would be "off" and the program would go to "yes" output and end or exit the program. If the program is not "off", the microprocessor 11 then goes to Step 2.

STEP 2. At this step, the microprocessor 11 monitors the status of the reed switch 16 and then goes on to Step 3.

STEP 3. Here the microprocessor 11 determines whether the reed switch 16 is still closed. If it is, the program goes on to Step 4.

STEP 4. Here the microprocessor 11 determines whether more than 6 seconds have elapsed. If "no" the program loops back to Step 2. If "yes" the program goes on to Step 10.

STEP 5. If at Step 3 the reed switch is not still closed, the program or microprocessor 11 determines whether it has been closed for 2 seconds. If "yes" the program goes on to Step 6.

STEP 6. Here the program turns off the neural stimulating apparatus 10 and ends or exits the program.

STEP 7. If the answer to Step 5 was "no" the microprocessor 11 then determines whether the switch 16 had been closed for less than 1 second. If the answer is "no" the microprocessor ends or exits the program.

STEP 8. If the answer is "yes", the neural stimulator is turned on and the microprocessor 11 goes on to Step 9.

STEP 9. Here the current amplitude is returned to the originally programmed value and from there the microprocessor 11 ends or exits the program.

STEP 10. If at Step 5 the switch 16 had been closed for more than 6 seconds, the microprocessor 11 goes on to Step 10 and a determination is made as to whether or not the output current is on. If "yes", the microprocessor 11 exits or ends the program. If "no" it goes on to Step 11.

STEP 11. At this step, a determination is made if the magnetic ramp function, i.e., ramp 24, is set. If "no" the microprocessor 11 ends or exits the program. If "yes" the microprocessor 11 goes on to Step 12.

STEP 12. Here the output current is reset to zero.

STEP 13. Here the microprocessor 11 determines whether or not the reed switch 16 is still closed. If "no" the microprocessor 11 ends or exits the program. If "yes" the microprocessor 11 goes on to Step 14.

STEP 14. At this step, the microprocessor 11 causes the value of the output current to increase in levels or steps with three amplitude bursts for each level of increase (such as the amplitude burst 30 and 33 shown in FIG. 4). This will occur until the magnet 20 is removed or the microprocessor 11 makes a determination in Step 15 that the upper level of current has been reached.

STEP 15. At Step 14 the microprocessor 11 is monitoring the increase in current amplitude and when it determines that the amplitude of the current has not reached the maximum amplitude of the current the microprocessor 11 loops back to the beginning of Step 13. If on the other hand, the microprocessor 11 determines that the maximum current of amplitude has been reached, the microprocessor ends or exits the program to stop further increases in output current level.

From the foregoing description, it will be apparent that the neural stimulating apparatus 10 of the present invention and the method for using same allow either the patient or the physician to alter the level of output current using an external magnet 20. Such use of the external magnet 20 for the predetermined period of time initiates an incrementally increasing output current under control of a program in an implanted microprocessor 11, allowing the patient to determine the effective level of output current for efficacious stimulation and then fix the level of the output current at that selected level. Further, the microprocessor 11 is programmed to limit the upper value of output current that can be supplied to electrodes adjacent nerves to be stimulated so that such output current cannot reach an unsafe level.

Further from the foregoing description, it will be apparent that modifications can be made to the apparatus 10 and method for using same without departing from the teachings of the present invention. Accordingly, the scope of the invention is only to be limited as necessitated by the accompanying claims.

I claim:

1. A neural stimulating system for permitting patient control of a neural stimulator within preset limits in response to an externally and manually applied magnetic field, said neural stimulating system comprising:

a magnet for use by the patient;

a magnetically controlled switch for implantation in a patient's body just beneath the patient's skin and for being positioned at a location in the body for selective closing by application of an external magnetic field as established by placing said magnet over the patient's skin adjacent said switch;

a neural stimulating electrode for implantation in a patient's spine adjacent the patient's spinal cord; and a neural stimulator including programmable electronic circuit means for implantation in a patient's body, such as adjacent said switch, said circuit means being electrically coupled to said magnetically controlled switch and to said neural stimulating electrode and said circuit means including means for generating [a selective] *neural stimulating* electrical output current *pulses of a selected magnitude* between a minimum level of [zero] current, programmed into said circuit means and a maximum level *of current* programmed [by a physician] into said circuit means in response to closing of and duration of the closure of said magnetically controlled switch, [which] *the* output current *pulses being* [is] supplied to said neural stimulating electrode, said means for generating [an] output current *pulses* including means for [generating] gradually[,] *and* incrementally [increasing] *changing the magnitude of the* neural stimulating electrical output current pulses, in response to the application of the externally applied magnetic field to said magnetically controlled switch for a predetermined period of time.

2. The system of claim 1 wherein said means for [generating gradually, incrementally increasing] *changing the magnitude of the* neural stimulating electrical output current pulses includes means for generating current pulses along a ramp function.

3. The system of claim 1 wherein said electronic circuit means [comprises] *comprise* means for detecting the electrical output current being generated at the time of removal of the externally applied magnetic field and the opening of said magnetic actuated switch and for maintaining said output current at the detected level.

4. The system of claim 3 wherein said implanted circuit means comprises a microprocessor coupled to said switch and to said current generating means.

5. The system of claim 4 wherein said microprocessor includes means for detecting the opening and closing of the magnetically actuated switch and means for turning the neural stimulator [or] *on* in response to closure of said switch for a first duration, means for turning the neural stimulator off in response to a closure of said switch for a second duration following immediately after said first duration, and means for initiating [an incrementally increasing] *said means for changing the magnitude of the* neural stimulator output current *pulses* in response to a closure of said switch for a third duration following immediately after said second duration.

6. A method for controlling, by a patient, the operation of a neural stimulating system including a magnet, a neural stimulator implanted in a patient's spine including current generating means, a microprocessor implanted beneath a patient's skin coupled to said current generating means and a magnetically responsive reed switch means implanted beneath a patient's skin and connected to the microprocessor, said method comprising the steps of:

manually causing, from a position exterior of a patient's body, closing of the reed switch means for a predetermined time period by holding the magnet adjacent said reed switch means for said predetermined time period;

generating output current pulses from the neural stimulator;

and causing the output current pulses from the neural stimulator to increase incrementally from a minimum *programmed level* [value of 0] so long as the reed switch means is closed beyond the predetermined time period and only until a certain current level is reached, which is the lesser of a level of output current that interrupts human body generated pain pulses and a maximum output current level of the neural stimulator preprogrammed by a physician into the microprocessor;

said step of causing the output current pulses to increase including the step of utilizing means for gradually and incrementally increasing the output current pulses to increase the output current pulses incrementally to successively higher current values.

7. The method according to claim 6 wherein said predetermined time period is at least 6 seconds.

8. The method of claim 6 wherein said step of incrementing the output current pulses is carried out over a time period of a ramp function for current values [from 0 milliamps] *up* to a maximum [of 8.9 milliamps] *current level.*

9. The method of claim 6 wherein said step of incrementing the output current pulses is carried out according to a ramp function which is started at a time approximately 6 seconds after initial closing of the switch means and is continued for a duration of 30 seconds for a total switch means closed period of 36 seconds.

10. The method of claim 6 wherein said step of causing the output current pulses from the neural stimulator to increase includes the step of gradually and incrementally increasing the output current pulses along the slope of a ramp function from [0] *said minimum programmed output current level* to said maximum programmed output current level.

11. The method of claim 10 wherein said step of incrementally increasing the output current pulses includes incrementally increasing the output current in steps of 0.12 milliamps per step along the ramp function.

12. The method of claim 10 wherein said ramp function has a duration of 30 seconds.

13. The method of claim 10 wherein said output current increases over the [timer] *time* period of said ramp function from [0] *said minimum programmed output current level* to a maximum [of 8.9 milliamps] *current level.*

14. The method of claim 6 wherein said step of incrementing the output current pulses in steps includes generating 3 bursts of output current pulses at one level followed by 3 bursts of current pulses at a next succeeding level approximately 0.12 milliamps above the preceding level.

15. The method of claim 14 where the step of generating 3 current pulses includes generating said current pulses over a time period of 0.024 seconds for each step increase in current.

16. The method of claim 10 wherein said step of incrementally increasing the output current pulses includes increasing the output current pulses over a time period of said ramp function from [0 milliamps] *said programmed minimum output current* to a maximum [of 8.9 milliamps] *current level.*

17. The method of claim 6 wherein said step of closing the switch means for a time period of more than 2 seconds and less than 6 seconds includes turning off the neural stimulator.

* * * * *